(12) United States Patent
Yahagi et al.

(10) Patent No.: US 12,109,363 B2
(45) Date of Patent: Oct. 8, 2024

(54) FIXING DEVICE AND RESPIRATOR

(71) Applicant: NIHON KOHDEN CORPORATION, Tokyo (JP)

(72) Inventors: Hiroaki Yahagi, Tokorozawa (JP); Isao Matsubara, Tokorozawa (JP); Satoru Watanabe, Okaya (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 916 days.

(21) Appl. No.: 17/058,498

(22) PCT Filed: May 28, 2019

(86) PCT No.: PCT/JP2019/021091
§ 371 (c)(1),
(2) Date: Nov. 24, 2020

(87) PCT Pub. No.: WO2019/230721
PCT Pub. Date: Dec. 5, 2019

(65) Prior Publication Data
US 2021/0196917 A1   Jul. 1, 2021

(30) Foreign Application Priority Data
May 29, 2018   (JP) ................................ 2018-102306

(51) Int. Cl.
*A61M 16/08*   (2006.01)
*A61B 90/50*   (2016.01)
(Continued)

(52) U.S. Cl.
CPC ......... *A61M 16/0816* (2013.01); *A61B 90/50* (2016.02); *A61M 16/0875* (2013.01);
(Continued)

(58) Field of Classification Search
CPC .............. A61M 16/08; A61M 16/0816; A61M 16/0875; A61M 16/16; A61M 2016/003;
(Continued)

(56) References Cited

U.S. PATENT DOCUMENTS 4,707,906 A * 11/1987 Posey ..................... F16L 3/223
24/339
5,184,601 A    2/1993 Putman
(Continued)

FOREIGN PATENT DOCUMENTS

CN    213191926 U    5/2021
JP    2001129087 A    5/2001
(Continued)

OTHER PUBLICATIONS

Communication dated Jan. 11, 2022 issued by the Japanese Patent Office in application No. 2018-102306.
(Continued)

*Primary Examiner* — Joseph D. Boecker
(74) *Attorney, Agent, or Firm* — Sughrue Mion, PLLC

(57) ABSTRACT

A fixing device in which the direction of a tube can be easily fine-adjusted is provided. A fixing device has: an arm portion which extends in the X direction; a fixation portion which is to fix a tube; and a rotation portion which is disposed between the arm portion and the fixation portion, and which rotates the fixation portion about the X direction.

9 Claims, 7 Drawing Sheets

(51) Int. Cl.
*A61M 16/00* (2006.01)
*A61M 16/16* (2006.01)
*F16L 3/015* (2006.01)
*F16L 3/13* (2006.01)
*F16L 3/237* (2006.01)
*F16M 11/14* (2006.01)
*F16M 13/02* (2006.01)

(52) U.S. Cl.
CPC ....... *A61M 2016/003* (2013.01); *A61M 16/16* (2013.01); *A61M 2209/08* (2013.01); *A61M 2209/082* (2013.01); *F16L 3/015* (2013.01); *F16L 3/13* (2013.01); *F16L 3/237* (2013.01); *F16M 11/14* (2013.01); *F16M 13/02* (2013.01); *F16M 2200/022* (2013.01)

(58) Field of Classification Search
CPC ........ A61M 2209/08; A61M 2209/082; A61M 5/14; A61M 5/1418; A61M 2025/02; A61M 2025/024; A61M 2025/028; A61M 39/08; A61M 39/10; A61M 39/12; A61M 39/28; A61M 39/1055; A61M 2039/087; A61M 25/02; F16L 3/015; F16L 3/13; F16L 3/237; F16L 3/1041; F16L 3/12; F16L 3/227; F16M 11/14; F16M 2200/022; F16M 13/02; H02G 3/32; Y10S 128/26; A61B 5/6835; A61B 5/6838; A61B 90/50; A61B 90/57; F16B 2/10; F16B 2/12; A62B 9/04; A62B 25/00; A62B 25/005
See application file for complete search history.

(56) References Cited

U.S. PATENT DOCUMENTS

| | | | | |
|---|---|---|---|---|
| 5,441,042 A | * | 8/1995 | Putman | B25J 9/042 600/102 |
| 5,897,199 A | * | 4/1999 | Norris | F21V 21/145 362/396 |
| 5,951,461 A | | 9/1999 | Nyo et al. | |
| 2002/0053345 A1 | | 5/2002 | Jafari et al. | |
| 2003/0116167 A1 | * | 6/2003 | Hooser | F16M 11/2021 128/912 |
| 2004/0103896 A1 | | 6/2004 | Jafari et al. | |
| 2004/0188578 A1 | * | 9/2004 | Turner | F16M 11/10 248/281.11 |
| 2005/0041048 A1 | * | 2/2005 | Hillman | F16M 11/08 345/905 |
| 2005/0087190 A1 | | 4/2005 | Jafari et al. | |
| 2007/0055291 A1 | | 3/2007 | Birkmeyer et al. | |
| 2008/0178882 A1 | * | 7/2008 | Christopher | A61M 16/0465 128/204.23 |
| 2011/0040305 A1 | | 2/2011 | Gomez et al. | |
| 2015/0007810 A1 | * | 1/2015 | Smith | A61M 15/00 128/200.14 |
| 2017/0112588 A1 | | 4/2017 | Bissing et al. | |
| 2017/0246417 A1 | * | 8/2017 | Kemps | A61M 15/009 |
| 2018/0200485 A1 | * | 7/2018 | Braham | A61M 16/0051 |

FOREIGN PATENT DOCUMENTS

| | | | | |
|---|---|---|---|---|
| JP | 200433550 A | | 2/2004 | |
| JP | 2008194504 A | | 8/2008 | |
| JP | 3204743 U | | 6/2016 | |
| JP | 6250847 B1 | * | 12/2017 | ............ A61M 16/08 |
| JP | 3233338 U | | 8/2021 | |
| WO | WO-0073691 A1 | * | 12/2000 | ........... E04H 4/1636 |

OTHER PUBLICATIONS

International Search Report dated Aug. 16, 2019 issued by the International Searching Authority in counterpart International Application No. PCT/JP2019/021091 (PCT/ISA/210).

International Written Opinion dated Aug. 16, 2019 issued by the International Searching Authority in counterpart International Application No. PCT/JP2019/021091 (PCT/ISA/237).

* cited by examiner

FIXING DEVICE AND RESPIRATOR

CROSS-REFERENCE TO RELATED APPLICATIONS

This application is a National Stage of International Application No. PCT/JP2019/021091 filed May 28, 2019, claiming priority based on Japanese Patent Application No. 2018-102306, filed May 29, 2018, the contents of all of which are incorporated herein by reference in their entirety.

TECHNICAL FIELD

The present invention relates to a fixing device and a respirator.

BACKGROUND ART

A respirator is attached to a patient who is difficult to perform spontaneous respiration, to assist respiration. A tube connects between a respirator and a mask which is attached to the patient. Usually, the tube is fixed by a fixing device (holder).

In this context, PTL 1 below discloses a hose holder for a respirator in which a tube is held by a metal spring member. According to the hose holder for a respirator, the tube (hose) can be appropriately held by the elastic force of the spring member.

CITATION LIST

Patent Literature

[PTL 1] Japanese Utility Model No. 3,204,743

SUMMARY OF INVENTION

Technical Problem

A tube for a respirator is requested that the tube is moved to a predetermined approximate position, and then the direction of the tube is finally fine-adjusted. In the holder disclosed in PTL 1, for example, the direction of the tube can be fine-adjusted by bending the tube, but there is a possibility that the tube is accidentally damaged.

It is an object of the invention to provide a fixing device and respirator in which the direction of a tube can be fine-adjusted while preventing the tube from being damaged.

Solution to Problem

A fixing device of a first aspect of the invention is a fixing device for fixing a tube for a medical apparatus. The fixing device has: an arm portion which extends in a long-axis direction; a fixation portion which is to fix the tube; and a rotation portion which is disposed between the arm portion and the fixation portion, and which allows the fixation portion to be rotated about the long-axis direction.

A respirator of a second aspect of the invention has the above-described fixing device, and a respirator body.

Advantageous Effects of Invention

The above-described fixing device and respirator have the rotation portion which rotates the fixation portion about the long-axis direction, and therefore the direction of the tube can be easily fine-adjusted. Moreover, the fixation portion is rotated in the state where the fixation portion fixes the tube. Therefore, it is possible to prevent the tube from being damaged. As a result, it is possible to provide a fixing device and respirator in which the direction of a tube can be fine-adjusted while preventing the tube from being damaged.

DESCRIPTION OF EMBODIMENTS

Figure 1:
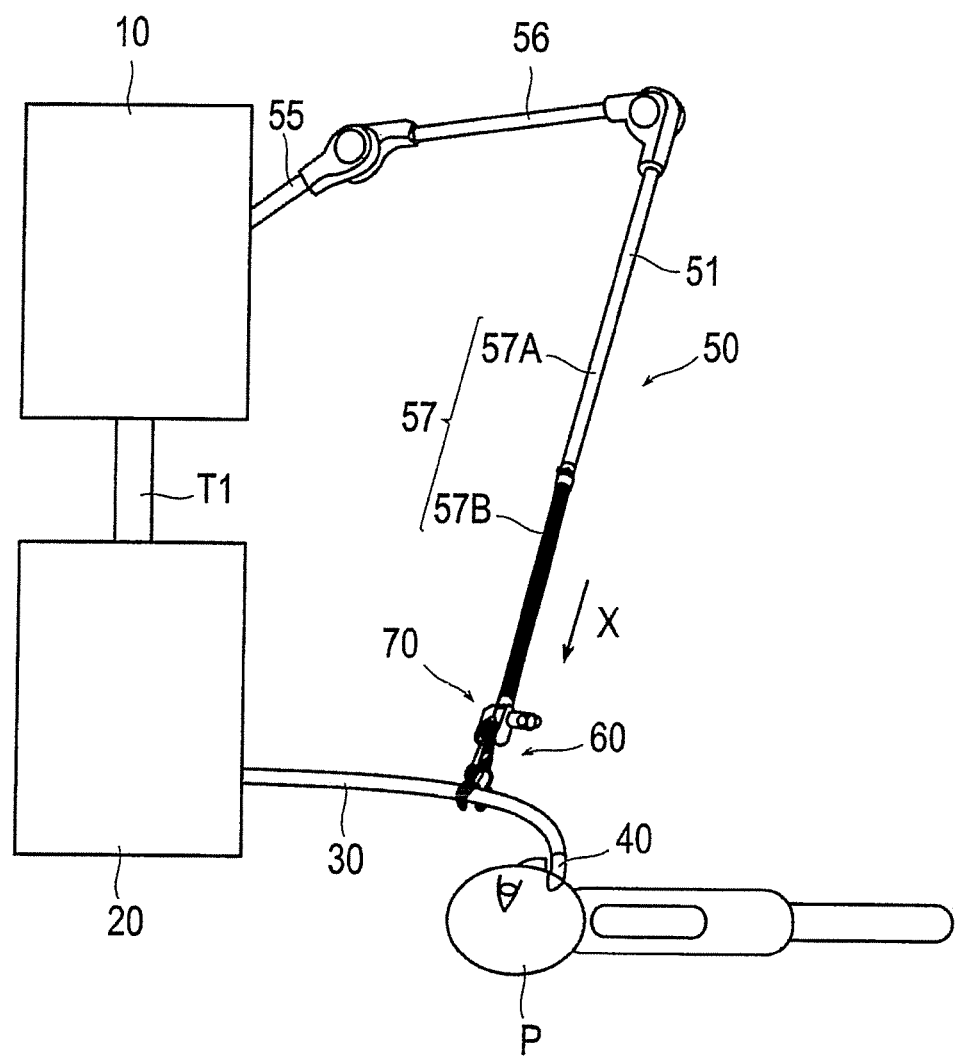
FIG. 1 is a diagram illustrating a respirator of an embodiment.

An embodiment of the invention will be described with reference to the drawings. In the description of the drawings, identical components are denoted by the same reference numerals, and duplicated description is omitted. In the drawings, the dimension ratios are exaggerated for the sake of convenience in description, and may be sometimes different from the actual ratios.

Figure 2:
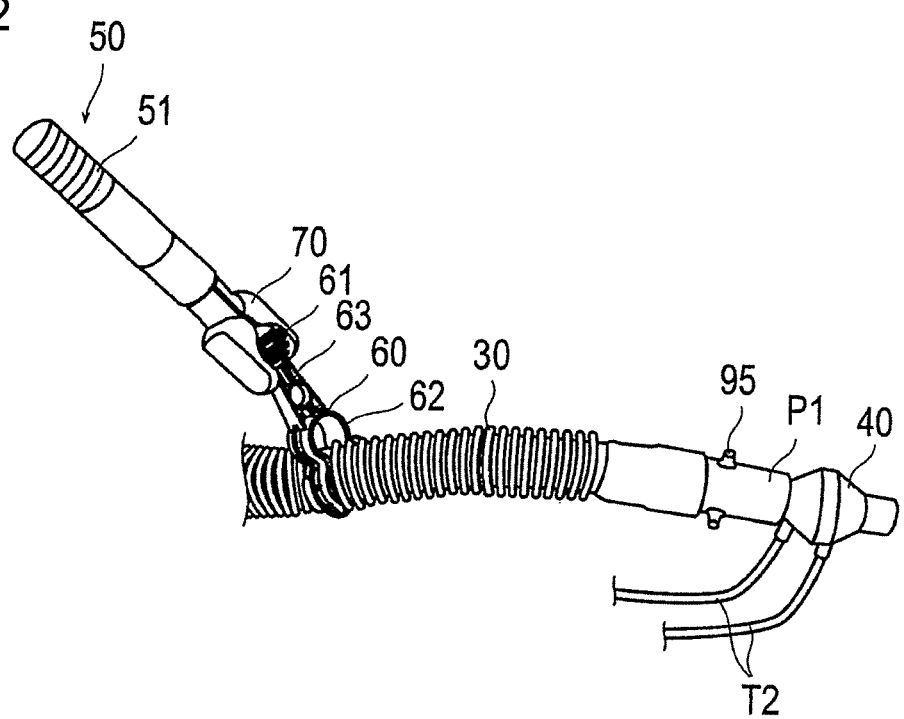
FIG. 2 is a diagram illustrating the configurations of a tube, a connection portion, and a connecting pipe.
Figure 3:
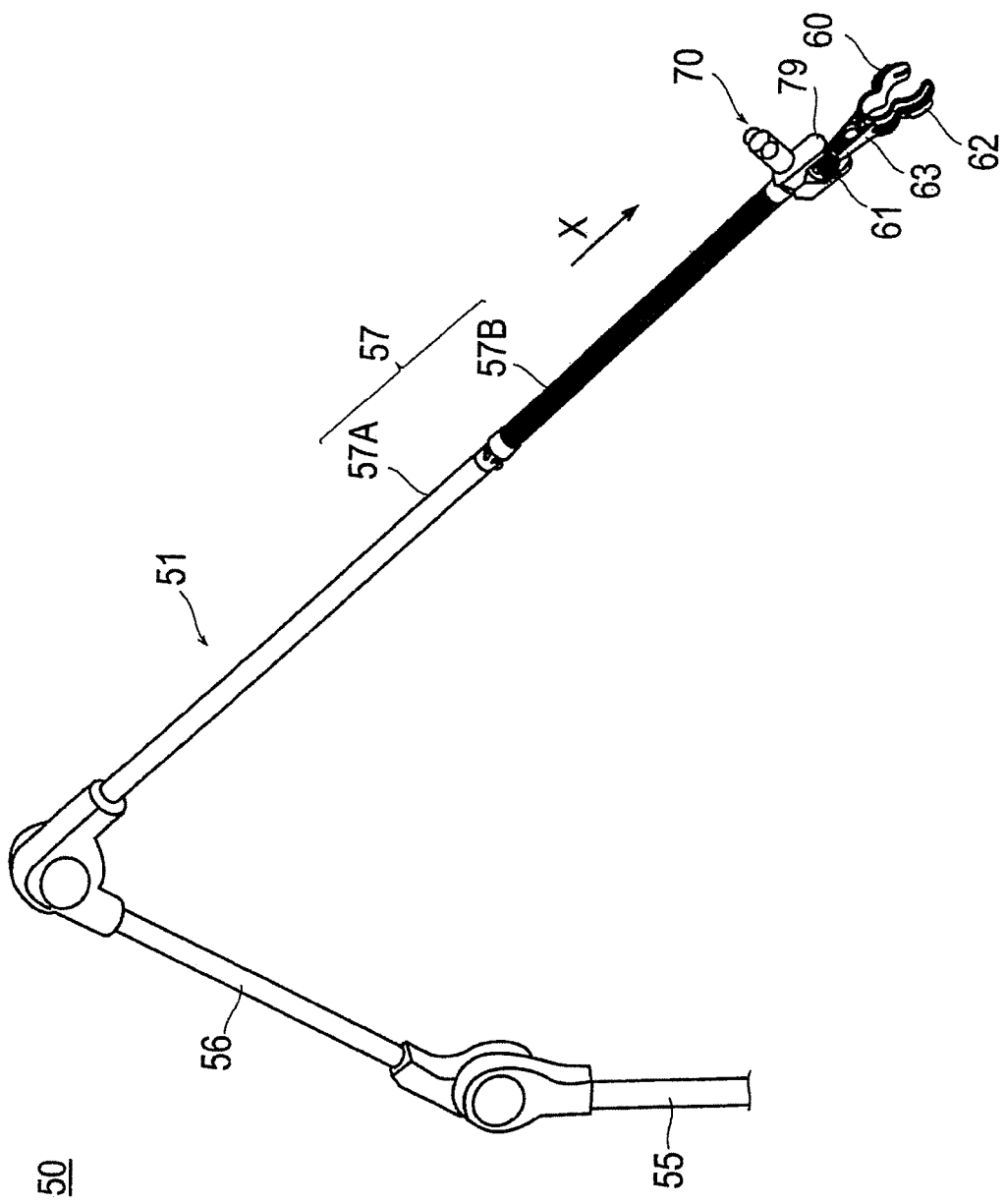
FIG. 3 is a perspective view illustrating an arm portion, a rotation portion, and a fixation portion.
Figure 4:
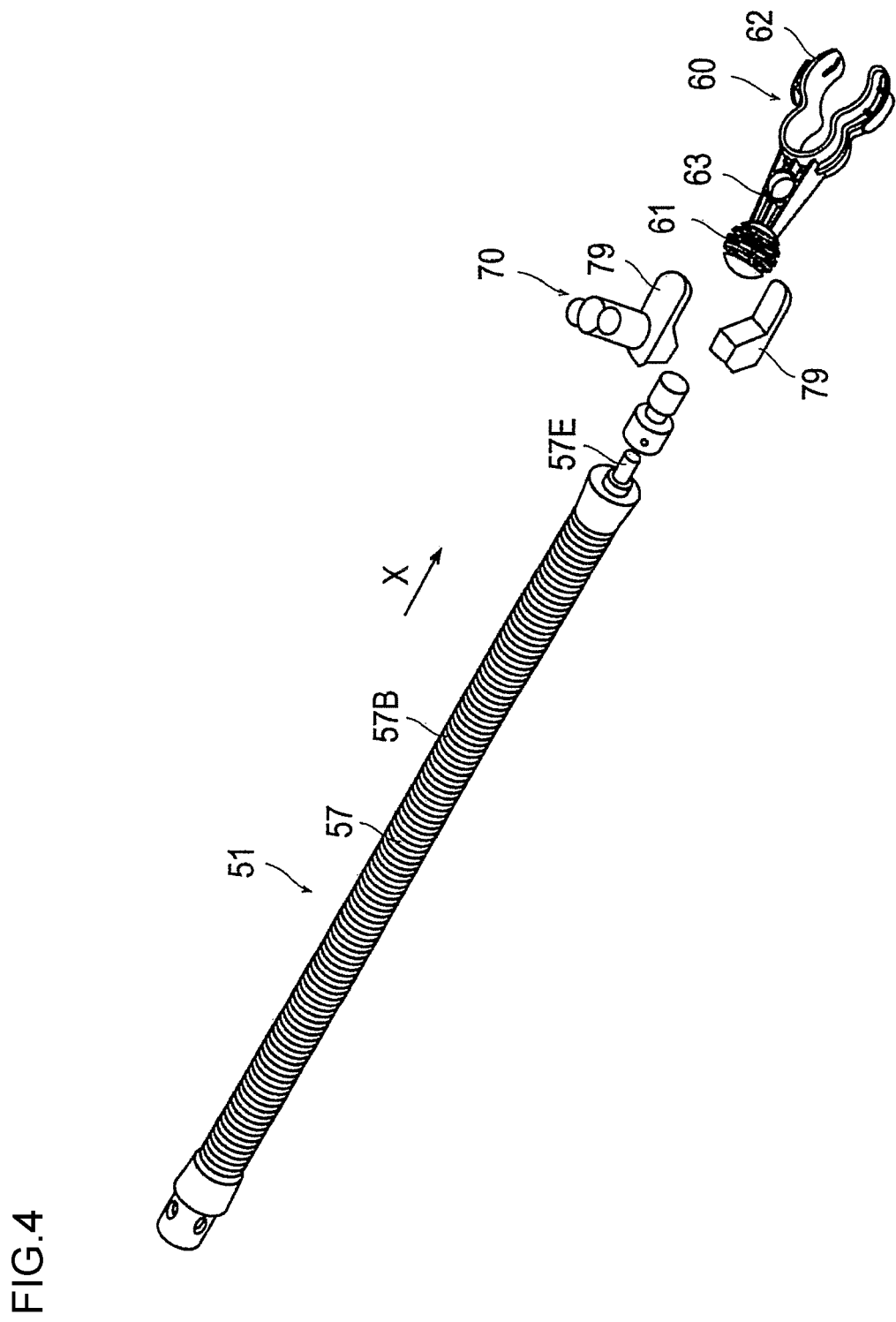
FIG. 4 is an exploded perspective view illustrating the arm portion, the rotation portion, and the fixation portion.
Figure 5:
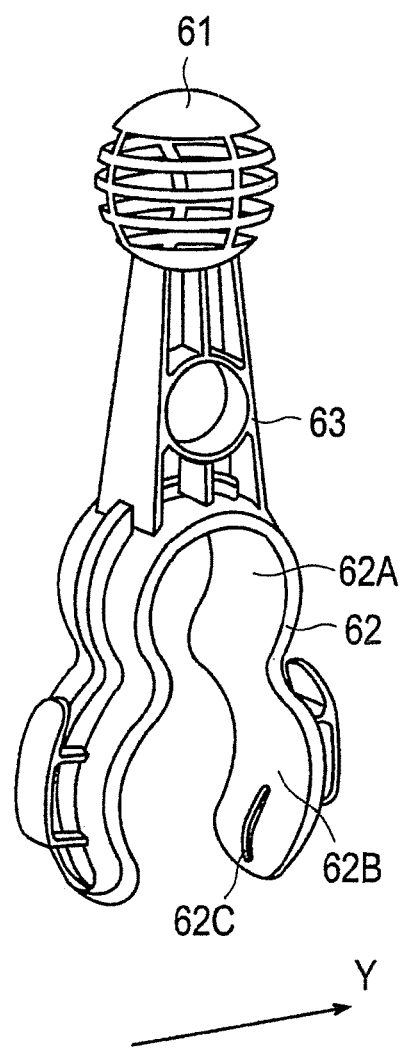
FIG. 5 is a perspective view illustrating the fixation portion in the embodiment.
Figure 6:
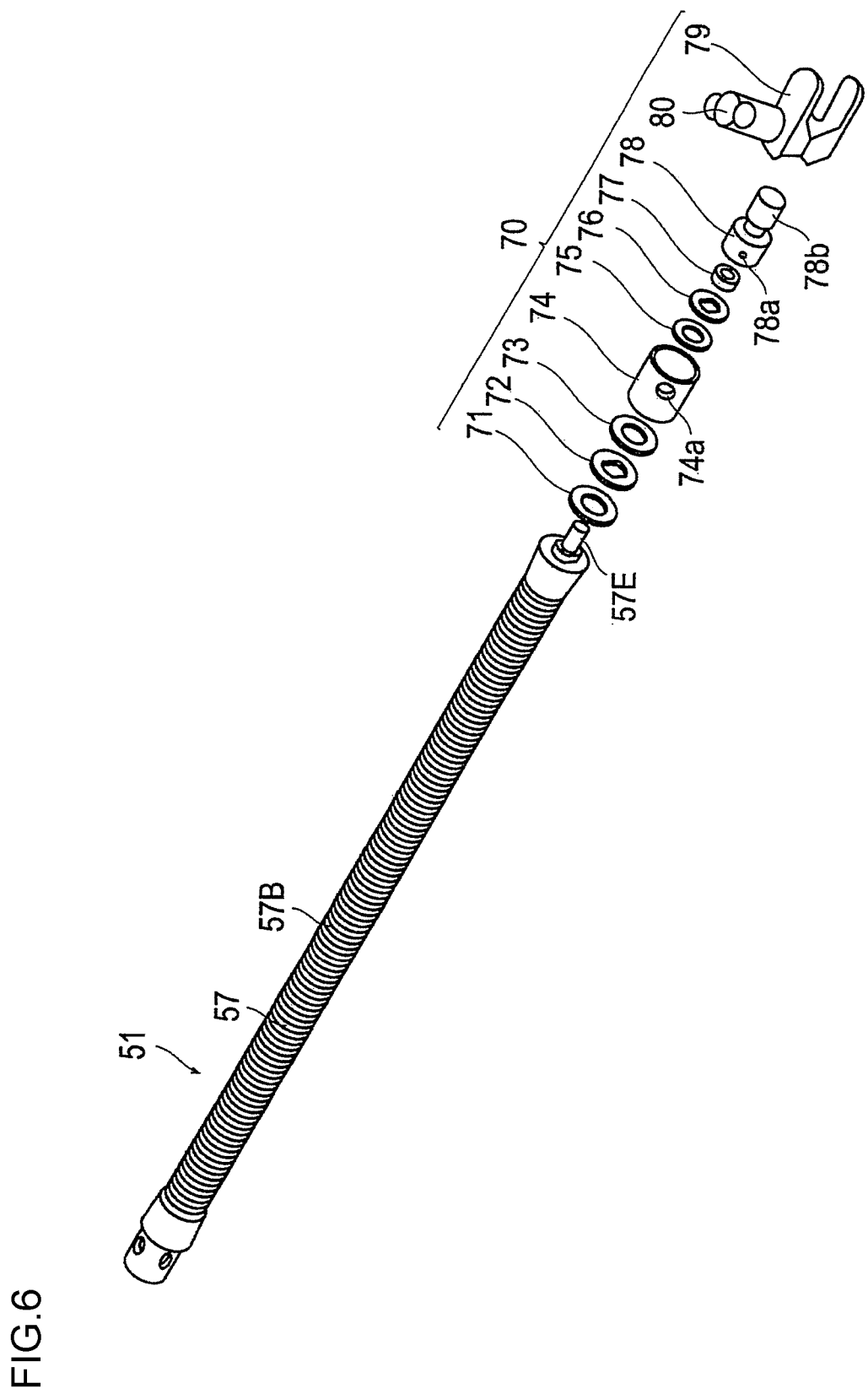
FIG. 6 is an exploded perspective view illustrating the rotation portion.

FIG. 1 is a diagram illustrating a respirator 1 of the embodiment, FIG. 2 is a diagram illustrating the configurations of a tube 30, a connection portion 40, and a connecting pipe P1, FIG. 3 is a perspective view illustrating an arm portion 51, a rotation portion 70, and a fixation portion 60, FIG. 4 is an exploded perspective view illustrating the arm portion 51, the rotation portion 70, and the fixation portion 60, FIG. 5 is a perspective view illustrating the fixation portion 60 in the embodiment, and FIG. 6 is an exploded perspective view illustrating the rotation portion 70.

As illustrated in FIGS. 1 and 2, the respirator 1 may include the respirator body 10, a heating humidifier 20, the tube 30, the connection portion 40, and a fixing device 50.

The respirator body 10 outputs oxygen or the air. The respirator body 10 is configured by a flow sensor, an exhalation valve, an inspiration valve, a safety valve, an oxymeter, an insufflation mechanism, a blender, a power supply cord, etc. The respirator body 10 is configured in a usual manner, and therefore a detailed description thereof is omitted.

The heating humidifier 20 causes humidified water to contact with the oxygen or air which is output from the respirator body 10, thereby heating and humidifying the oxygen or the air. The heating humidifier 20 is connected to the respirator body 10 through a connection tube T1.

The tube 30 is connected to the heating humidifier 20. The tube 30 include a bellows-like hose. The oxygen or air which is heated and humidified in the heating humidifier 20 flows through the interior of the tube 30.

As illustrated in FIG. 2, the connection portion 40 is connected to the front end of the tube 30 through the connecting pipe P1.

The connecting pipe P1 is connected to the tube 30. The method of connecting the connecting pipe P1 to the tube 30 is not particularly limited, but for example the connection is performed by fitting. In the connecting pipe P1, a discharge hole 95 for discharging breath exhaled by the patient P to the outside is disposed.

As illustrated in FIG. 2, the connection portion 40 is connected to the connecting pipe P1. The side of the connection portion 40 which is opposite to the side that is connected to the connecting pipe P1 is connected to a mask (not illustrated) to be attached to the patient P. The method of connecting the connection portion 40 to the connecting pipe P1 and the mask is not particularly limited, but for example the connections may be performed by fitting.

A flow sensor tube T2 is connected to the connection portion 40, so that the flow amount of the oxygen or air which flows in the mask can be measured.

As illustrated in FIGS. 1 and 2, the fixing device 50 grips and fixes the tube 30, and applies an adequate torque to the tube, thereby fine-adjusting the rotation direction of the tube 30 about the X direction (see FIG. 3).

As illustrated in FIGS. 3 and 4, the fixing device 50 may include the arm portion 51, the fixation portion 60, and the rotation portion 70.

As illustrated in FIG. 3, the arm portion 51 may include a first arm portion 55, a second arm portion 56, and a third arm portion 57.

As illustrated in FIG. 1, the first arm portion 55 is fixed to the respirator body 10. The second arm portion 56 is connected to the first arm portion 55 so as to be movable with respect to the first arm portion. Each of the first arm portion 55 and the second arm portion 56 is configured as a rigid member.

The third arm portion 57 is connected to the second arm portion 56 so as to be movable with respect to the second arm portion. As illustrated in FIGS. 3 and 4, the third arm portion 57 is configured so as to elongate in the long-axis direction (X direction). As illustrated in FIG. 3, the third arm portion 57 may include a pipe portion 57A which is configured as a rigid member, and a flexible arm 57B which is configured so as to be easily deformed. In this way, the third arm portion 57 has the flexible arm 57B, and therefore the position of the fixation portion 60 can be adjusted by using the flexible arm 57B. Consequently, the position at which the tube 30 is fixed by the fixation portion 60 can be adjusted.

The fixation portion 60 fixes the tube 30 as illustrated in FIG. 1. As illustrated in FIG. 5, the fixation portion 60 may include a projecting part 61 which is configured into a spherical shape, a placing part 62 in which the tube 30 is to be placed, and a connecting part 63 through which the projecting part 61 and the placing part 62 are connected to each other.

As illustrated in FIGS. 3 and 4, the projecting part 61 is clamped by a holding part 79 of the rotation portion 70 which will be described later.

As illustrated in FIG. 5, the placing part 62 is configured into a substantially U-like shape, and the tube 30 can be placed in the part by means of an elastic force. The placing part 62 has a two-stage configuration (reference numerals 62A and 62B) so that two tubes 30 having different sizes can be placed in the part. According to the configuration, a tube 30 for an adult and/or tube 30 for a child which have different sizes can be placed in the placing part.

A non-slip part 62C which prevents the tube 30 from slipping is formed inside the placing part 62. The non-slip part 62C is disposed so as to be inward projected toward the radially inner side. The width of the non-slip part 62C has a size which allows the non-slip part to be fitted into a groove part of the tube 30 that is formed into a bellows-like shape.

In the embodiment, the flow sensor tube T2 can be placed in a place of the placing part 62 which is designated by the reference numeral 62A, and the tube 30 can be placed in a place of the placing part 62 which is designated by the reference numeral 62B.

As illustrated in FIG. 6, the rotation portion 70 may include, in a sequence starting from the side of the flexible arm 57B, a conical washer (the metal plate) 71, a first oval washer 72, a first POM washer (the first plate-like member) 73, a hose and rotation receiver 74, a second POM washer (the second plate-like member) 75, a second oval washer 76, a hexagonal nut 77, a hose receiving rotating part 78, the holding part 79, and an adjusting part 80.

The conical washer 71 includes a disc washer. The conical washer 71 has a spring characteristic, and provides the hose and rotation receiver 74 with an appropriate elastic force to cause the hose and rotation receiver to have an adequate rotation force. The conical washer 71 is inserted onto a male thread 57E of the flexible arm 57B so that the convex part (the left side) of the conical washer 71 is on the side of the flexible arm 57B. In the above embodiment, the conical washer 71 is metal plate, but the conical washer 71 may have other shapes including an inclined plate shape or a conical shape.

The first oval washer 72 transmits the elastic force of the conical washer 71 to the first POM washer 73. The first oval washer 72 is placed in order to suppress the rotation of the conical washer 71. The member which exerts these two functions is not limited to the first POM washer, and for example a metal member may be used as far as it can exert the same or similar functions.

The first POM washer 73 is disposed in order to reduce the friction force generated when the hose and rotation receiver 74 is rotated.

The hose and rotation receiver 74 is rotated in synchronization with the hose receiving rotating part 78. A through hole 74a is formed in the side surface of the hose and rotation receiver 74. The hose and rotation receiver 74 has a hollow shape which extends in the axial direction.

The second POM washer 75 is disposed in order to reduce the friction force generated when the hose and rotation receiver 74 is rotated.

The second oval washer 76 protects the second POM washer 75 from the force exerted by the hexagonal nut 77.

The hexagonal nut 77 is fixed so as to apply an adequate torque to the male thread 57E of the flexible arm 57B.

The hose receiving rotating part 78 is rotated in synchronization with the hose and rotation receiver 74. A female thread 78a is formed on the side surface of the hose receiving rotating part 78. The hose receiving rotating part 78 and the hose and rotation receiver 74 are fastened together by a screw which is not illustrated, thereby coupling the hose and rotation receiver 74 to the hose receiving rotating part 78.

The holding part 79 is configured so as to be able to clamp together a convex part 78b of the hose receiving rotating part 78 and the projecting part 61. When the width of the holding part 79 is reduced by the adjusting part 80, a state where the convex part 78b and the projecting part 61 are clamped together is produced, and, when the width of the holding part 79 is increased by the adjusting part 80, a state where the clamping is cancelled is caused.

According to the thus configured rotation portion 70, the hexagonal nut 77 is fixed so as to apply an adequate torque to the male thread 57E of the flexible arm 57B, and therefore the direction of the tube 30 can be fine-adjusted while preventing the fixation portion 60 from being unintentionally rotated.

When the thus configured fixing device 50 is to be used, first, the angle of the flexible arm 57B, that of the projecting part 61 with respect to the rotation portion 70, and the position where the fixation portion 60 fixes the tube 30 are appropriately adjusted, and the tube 30 is placed at a predetermined approximate position. Thereafter, an adequate torque is applied to the rotation portion 70 to rotate the fixation portion 60 about the X direction, thereby fine-adjusting the position of the tube 30.

As described above, the fixing device 50 of the embodiment fixes the tube 30 for a medical apparatus. The fixing device 50 has: the arm portion 51 which elongates in the long-axis direction (X direction); the fixation portion 60 which is to fix the tube 30; and the rotation portion 70 which is disposed between the arm portion 51 and the fixation portion 60, and which rotates the fixation portion 60 about the long-axis direction. The thus configured fixing device 50 has the rotation portion 70 which rotates the fixation portion 60 about the long-axis direction, and therefore the direction of the tube 30 can be easily fine-adjusted. Moreover, the fixation portion 60 is rotated in the state where the fixation portion 60 fixes the tube 30, and therefore it is possible to prevent the tube 30 from being damaged. As a result, it is possible to provide the fixing device 50 in which the direction of the tube 30 can be fine-adjusted while preventing the tube 30 from being damaged.

The rotation portion 70 has: the holding part 79 which can clamp the fixation portion 60; the hose receiving rotating part 78 which is clamped by the holding part 79; the hose and rotation receiver 74 which is disposed between the hose receiving rotating part 78 and the arm portion 51, and which is rotated in synchronization with the hose receiving rotating part 78; the conical washer 71 which is disposed between the hose and rotation receiver 74 and the arm portion 51, which provides the hose and rotation receiver 74 with an appropriate elastic force, and in which the through hole that passes through the conical washer in the long-axis direction of the arm portion 51 is formed; the first POM washer 73 which is disposed between the conical washer 71 and the hose and rotation receiver 74, which reduces the friction force generated when the hose and rotation receiver 74 is rotated, and in which the through hole that passes through the first POM washer in the long-axis direction of the arm portion 51 is formed; and the second POM washer 75 which is disposed between the hose and rotation receiver 74 and the hose receiving rotating part 78, which reduces the friction force generated when the hose and rotation receiver 74 is rotated, and in which the through hole that passes through the second POM washer in the long-axis direction of the arm portion 51 is formed. According to the thus configured fixing device 50, when the worker applies an adequate torque to the rotation portion 70, the fixation portion 60 is rotated about the X direction. Therefore, the direction of the tube 30 can be fine-adjusted while preventing the fixation portion 60 from being unintentionally rotated.

Moreover, the fixation portion 60 has the projecting part 61 which is configured into a spherical shape, and the holding part 79 clamps the projecting part 61. According to the thus configured fixing device 50, the fixation portion 60 is allowed to move in an arbitrary direction, and therefore the position of the fixation portion 60 with respect to the rotation portion 70 is easily adjusted.

The fixation portion 60 includes the placing part 62 in which the tube 30 is to be placed. According to the thus configured fixing device 50, the tube 30 can be preferably placed in the fixation portion 60.

Moreover, the placing part 62 has the two-stage configuration so that two tubes 30 having different sizes can be placed in the part. According to the thus configured fixing device 50, a tube 30 for an adult or tube 30 for a child which have different sizes can be placed in the placing part.

The non-slip part 62C which is inward projected toward the radially inner side is formed inside the placing part 62. According to the thus configured fixing device 50, the tube 30 can be preferably prevented from slipping.

The fixing device 50 fixes the tube 30 for a respirator. The thus configured fixing device 50 can be preferably used in the respirator 1.

As described above, the respirator 1 of the embodiment has the above-described fixing device 50, and the respirator body 10. According to the thus configured respirator 1, the direction of the tube 30 can be fine-adjusted while preventing the tube 30 from being damaged.

The invention is not limited to the above-described embodiment, but can be variously modified within the scope of the appended claims.

Figure 7:
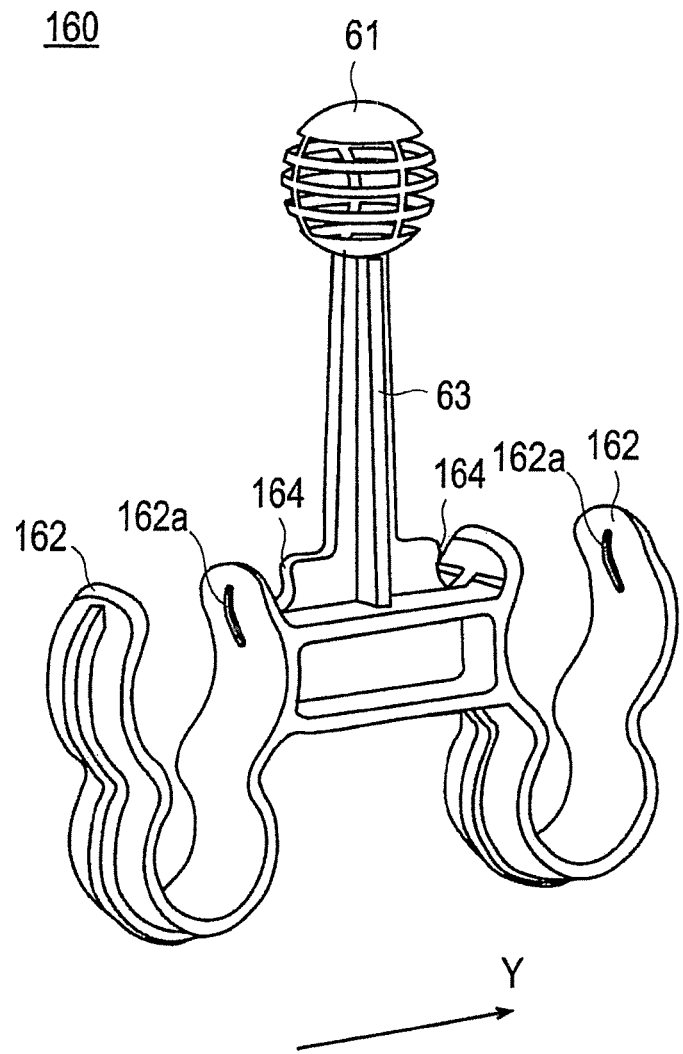
FIG. 7 is a perspective view illustrating the fixation portion in a modification.

In the embodiment, for example, the fixation portion 60 has the placing part 62 the number of which is one in the width direction (Y direction) as illustrated in FIG. 5. As illustrated in FIG. 7, however, a fixation portion 160 may include two placing parts 162 which are arranged in the width direction. The configuration can cope with also a respirator which includes two tubes, respectively, for exhalation and inspiration circuits. In this case, non-slip parts 162a may be formed in two placing parts 162, respectively. The fixation portion 160 may further include placement parts 164 in which flow sensor tubes T2 are to be placed, respectively. According to the configuration, the flow sensor tubes T2 may preferably bundled together, and it is possible to prevent the flow sensor tubes T2 from interrupting the work.

In the embodiment, as illustrated in FIG. 5, the placing part 62 has the two-stage configuration (the reference numerals 62A and 62B) so that two tubes 30 having different sizes can be placed in the part. However, the placing part may have a one-stage configuration so that one tube is placed in the placing part.

In the embodiment, the non-slip part 62C which is inward projected toward the radially inner side is formed inside the placing part 62. However, a non-slip part may not be formed inside the placing part.

INDUSTRIAL APPLICABILITY

This invention can be applied to provide a fixing device and respirator in which the direction of a tube can be fine-adjusted while preventing the tube from being damaged.

REFERENCE SIGNS LIST 1 respirator,
10 respirator body,
30 tube,
50 fixing device,
51 arm portion,
57E male thread,
60, 160 fixation portion,
61 projecting part, 62 placing part,
62C, 162a non-slip part,
164 placement part,
70 rotation portion,
71 conical washer (metal plate),
72 first oval washer,
73 first POM washer (first plate-like member),
74 hose rotation receiver,
75 second POM washer (second plate-like member),
76 second oval washer,
77 hexagonal nut,
78 hose receiving rotating part,
79 holding part,
80 adjusting part,
T2 flow sensor tube.

The invention claimed is:

1. A fixing device for fixing a tube for a medical apparatus comprising:
an arm portion that extends in a long-axis direction;
a fixation portion that is to fix a tube; and
a rotation portion that is disposed between the arm portion and the fixation portion directly on the long-axis of the arm portion and that allows the fixation portion to be rotated about the long-axis direction of the arm portion;
wherein the rotation portion includes:
a holding part that is capable of holding the fixation portion;
a hose receiving rotating part that is held by the holding part,
a hose rotation receiver that is disposed between the hose receiving rotating part and the arm portion, and that is rotated in synchronization with the hose receiving rotating part;
a metal plate which is disposed between the hose rotation receiver and the arm portion, which provides the hose rotation receiver with an elastic force, and in which a through hole that passes through the metal plate in the long-axis direction of the arm portion is formed;
a first plate-like member which is disposed between the metal plate and the hose rotation receiver, which reduces the friction force generated when the hose rotation receiver is rotated, and in which a through hole that passes through the first plate-like member in the long-axis direction of the arm portion is formed; and
a second plate-like member which is disposed between the hose rotation receiver and the hose receiving rotating part, which reduces the friction force generated when the hose rotation receiver is rotated, and in which a through hole that passes through the second plate-like member in the long-axis direction of the arm portion is formed.

2. The fixing device according to claim 1, wherein the fixation portion has a projecting part which is configured into a spherical shape, and
the holding part holds the projecting part.

3. The fixing device according to claim 1, wherein the fixation portion includes a placing part in which the tube is to be placed.

4. The fixing device according to claim 3, wherein the placing part has a two-stage configuration including a first stage and a second stage aligned directly on the long-axis direction of the arm portion so that a first tube having a first size is capable of being placed in the first stage of the placing part in a first state and a second tube of a second size is capable of being placed in the second stage of the placing part in a second, different state.

5. The fixing device according to claim 3, wherein a non-slip part that is disposed to be inward projected toward a radially inner side is formed inside the placing part.

6. The fixing device according to claim 3, wherein the fixation portion includes two placing parts arranged in a width direction.

7. The fixing device according to claim 1, wherein the fixation portion further includes a placement part in which a flow sensor tube for measuring a flow amount of air or oxygen in the tube is to be placed.

8. The fixing device according to claim 1, wherein the fixing device is to fix the tube for a respirator.

9. A respirator comprising:
the fixing device according to claim 1; and
a respirator body.

* * * * *